United States Patent
Jasper

(10) Patent No.: US 10,350,031 B2
(45) Date of Patent: Jul. 16, 2019

(54) METHOD AND APPARATUS FOR APPLYING CURVED VECTOR FORCES FOR ORTHODONTIC CORRECTIONS

(71) Applicant: James John Jasper, Portland, OR (US)

(72) Inventor: James John Jasper, Portland, OR (US)

( * ) Notice: Subject to any disclaimer, the term of this patent is extended or adjusted under 35 U.S.C. 154(b) by 0 days.

(21) Appl. No.: 15/843,414

(22) Filed: Dec. 15, 2017

(65) Prior Publication Data

US 2018/0140386 A1 May 24, 2018

Related U.S. Application Data

(63) Continuation-in-part of application No. 15/356,925, filed on Nov. 21, 2016, now abandoned.

(51) Int. Cl.
*A61C 7/36* (2006.01)

(52) U.S. Cl.
CPC ........................................ *A61C 7/36* (2013.01)

(58) Field of Classification Search
CPC ................................... A61C 7/08; A61C 7/36
USPC ......................................................... 433/8–17
See application file for complete search history.

(56) References Cited

U.S. PATENT DOCUMENTS

| | | | | |
|---|---|---|---|---|
| 4,708,646 A | * | 11/1987 | Jasper | A61C 7/36 433/19 |
| 6,120,289 A | * | 9/2000 | Cleary | A61C 7/36 433/19 |
| 6,394,799 B1 | * | 5/2002 | Testa | A61C 7/00 433/19 |
| 6,572,372 B1 | * | 6/2003 | Phan | A61C 7/00 433/18 |
| 2002/0192617 A1 | * | 12/2002 | Phan | A61C 7/00 433/6 |
| 2010/0139666 A1 | * | 6/2010 | Bonnaure | A61C 7/36 128/848 |
| 2010/0307511 A1 | * | 12/2010 | Meade | A61C 7/36 128/848 |
| 2011/0311936 A1 | * | 12/2011 | Marie-Catherine | A61C 7/36 433/19 |
| 2013/0236849 A1 | * | 9/2013 | Jasper | A61C 7/36 433/19 |
| 2014/0057222 A1 | * | 2/2014 | Kumar | A61C 7/36 433/19 |
| 2015/0245888 A1 | * | 9/2015 | Hasegawa | A61C 7/36 433/19 |
| 2016/0067014 A1 | * | 3/2016 | Kottemann | A61C 7/36 433/6 |
| 2017/0319297 A1 | * | 11/2017 | Cleary | A61C 7/36 |

* cited by examiner

*Primary Examiner* — Ralph A Lewis

(57) ABSTRACT

A method for the treatment of Class II and III malocclusions by applying curved intrusive vector forces to the dental arches. The apparatus is anchored in operational contact by a pair of sheaths that are form fit over some or all of the teeth in the upper and lower dental arches. The apparatus can be removed by the user and can be incorporated into both full and partial Class I malocclusion aligners. Most importantly, the apparatus does not require the use of braces affixed to the teeth and it has an adjustable pressure range of pushing force.

5 Claims, 7 Drawing Sheets

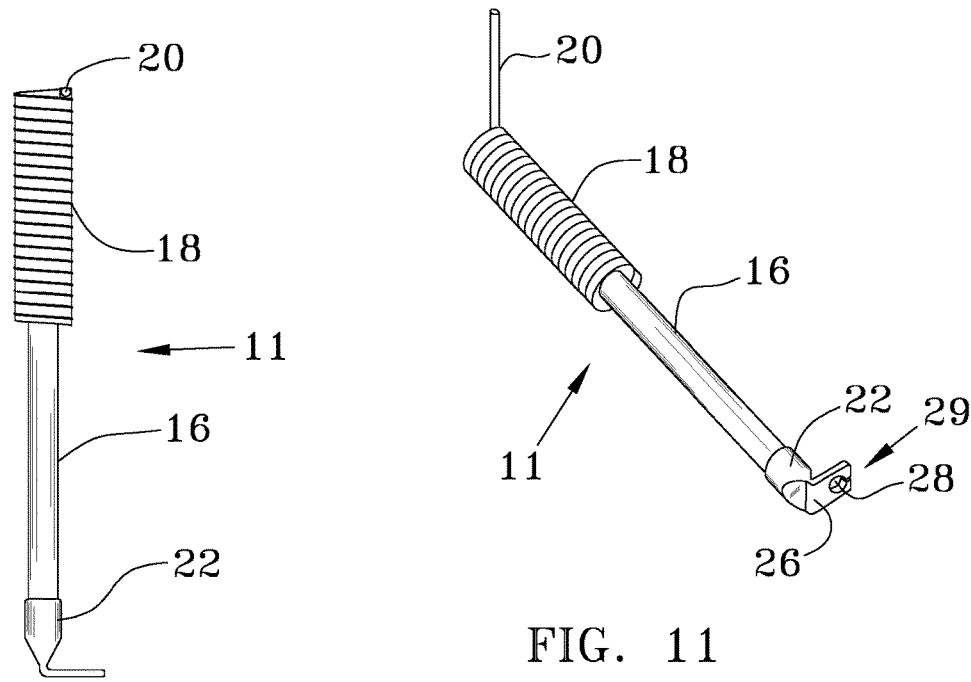
FIG. 10
FIG. 11
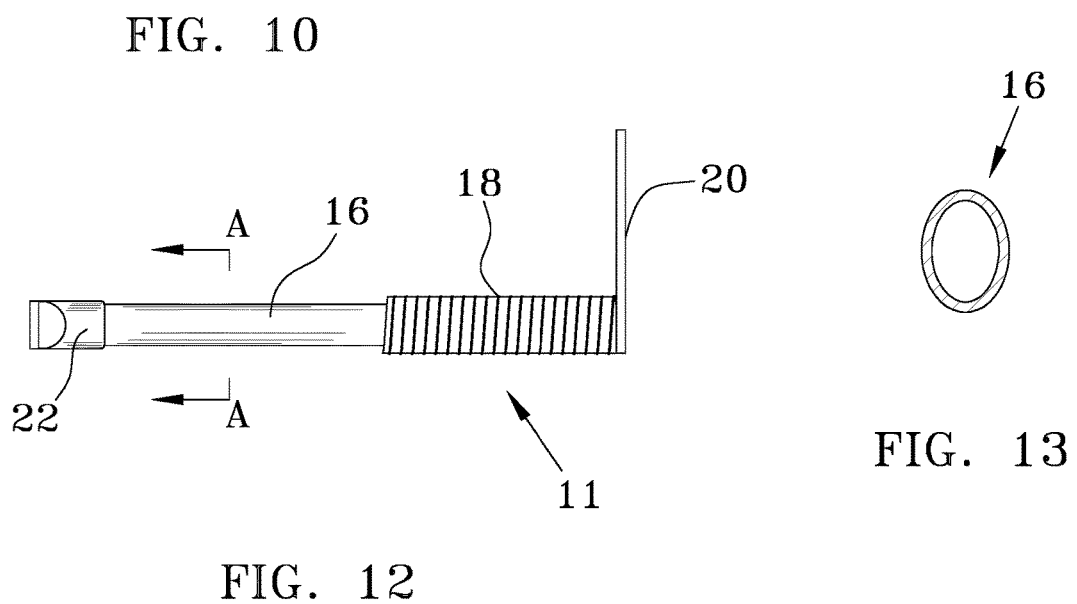
FIG. 12
FIG. 13

METHOD AND APPARATUS FOR APPLYING CURVED VECTOR FORCES FOR ORTHODONTIC CORRECTIONS

CLAIM FOR DOMESTIC PRIORITY

This application incorporates by reference and is a Continuation in Part of U.S. patent application Ser. No. 15/356,925 filed Nov. 21, 2016 and herein incorporates by reference all disclosed material and definitions therein.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to orthodontic appliances, and more particularly to the technology of temporary, vector force application devices for the correction of the misalignment of teeth between the upper dental arch and lower dental arch, whether it be overbite or underbite.

BACKGROUND

The incorrect positioning of teeth or the misalignment of teeth between the upper dental arch and lower dental arch are known as malocclusions. Malocclusions are categorized by dental health professionals in three classifications: Class I—the jaw relationship is normal but individual teeth (whether located on the upper or lower dental arch) have problems such as spacing, crowding, etc., and do not achieve a good fit with the corresponding teeth on the opposite arch. Class II—commonly referred to as an overbite, the upper jaw is not in proper position, and an increased projection of the upper teeth in front of the lower teeth results. This lack of contact between the front teeth allows them to keep erupting or extruding, from the gum line into the mouth until they contact something, usually the palate. This over-extrusion, especially of the lower front teeth, requires the orthodontist to place intrusive forces on these teeth during treatment. Finally, Class III—wherein the upper dental arch rests behind the lower dental arch when the mouth is closed, commonly referred to as an underbite.

Class 1 malocclusions are treated with braces (that is the combination of brackets, placed on individual teeth, and an archwire connecting each of the brackets) that are gradually adjusted to urge the movement of the teeth into their desired positions over a period of months or years. Class II or III malocclusions are also corrected slowly over an extended period of time, but by a vector force application apparatus that applies a low pulling or pushing pressure vector force to the offending jaw into its proper bite position. This vector appliance thus actually forces the jawbones and muscles to physically adapt or "learn" the correct bite positioning. Since commonly, Class I malocclusions are found in patients that also have Class II or Class III malocclusions, these misalignments of jaws and teeth are treated together wherein the brackets and/or archwires of the braces serve as the anchor point for the vector appliance.

There was a bite-correcting appliance known as the "Jasper Jumper" that gained popularity because of its low cost, adjustability, ease to repair and mostly because its results are garnered easily and in a short period of time. This is discussed in detail in U.S. Pat. No. 4,708,646. However, this was a non-removable bite-correcting appliance secured to braces and prone to structural failure. There were subsequent advances in this technology as detailed in U.S. Pat. Nos. 8,529,253, 8,721,326 and 8,905,755 incorporated herein by reference. These bite-correcting orthodontic appliances also attached directly to the elements of braces (i.e., brackets and archwires); flex in their distal 25-45% of their overall appliance length, to stay away from the food bolus; have a reduced profile for patient comfort; and introduce gentle intrusive force vectors to the patient's upper and lower teeth that are not along the appliance's axis but instead sweep in an arch to lift up on the front of the upper molar and down on the lower front teeth as the appliances try to return to their preinstalled (passive) state. They resulted in rapid, yet gentle changes unexpectedly reducing treatment times significantly.

However, once installed, these remained with the patient until removed by the orthodontist. This often precluded the wearer from participating in sports for period of time. Physical oral intimacy was also compromised. Furthermore, failures in the appliance required in-mouth repairs by an orthodontist which is costly, time consuming, uncomfortable and expensive.

Henceforth, an improved dental apparatus that can treat Class II or Class III malocclusions without the need for braces, that can be repaired outside of the patient's mouth, that can be temporarily removed by the patient for sports, eating etc. and that is inexpensive, would fulfill a long felt need in the dental industry. This new invention utilizes and combines known and new technologies in a unique and novel configuration to overcome the aforementioned problems and accomplish this.

BRIEF SUMMARY

In accordance with various embodiments, an orthodontic apparatus for the treatment of Class II and III malocclusions by the application of curved rather than linear intrusive vector forces is provided that can be temporarily removed by the user for sports, eating, intimacy and sleep; that can be repaired and cleaned outside of the mouth; that can be configured with either full or partial anchor sheaths; That can be configured to work with Class I malocclusion aligners: that do not require the use of braces affixed to the teeth; that have an adjustable pressure range optimally targeted for 3.5 ounces of pushing force; that can be used with bracing-only aligners that are not designed for any Class I malocclusion correction; that can be removed to accommodate other dental or mouth work; that offers minimal discomfort for the patient; and that offer a huge reduction in cost.

Various modifications and additions can be made to the embodiments discussed without departing from the scope of the invention. For example, while the embodiments described above refer to particular features, the scope of this invention also includes embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components.

FIG. 10 is a top view of the orthodontic vector force application means;

FIG. 11 is a right-side perspective view of the orthodontic vector force application means;

FIG. 12 is a left-side view of the orthodontic vector force application means;

FIG. 13 is an enlarged cross-section taken at the line designated A-A on FIG. 12;

DETAILED DESCRIPTION OF CERTAIN EMBODIMENTS

Figure 1:
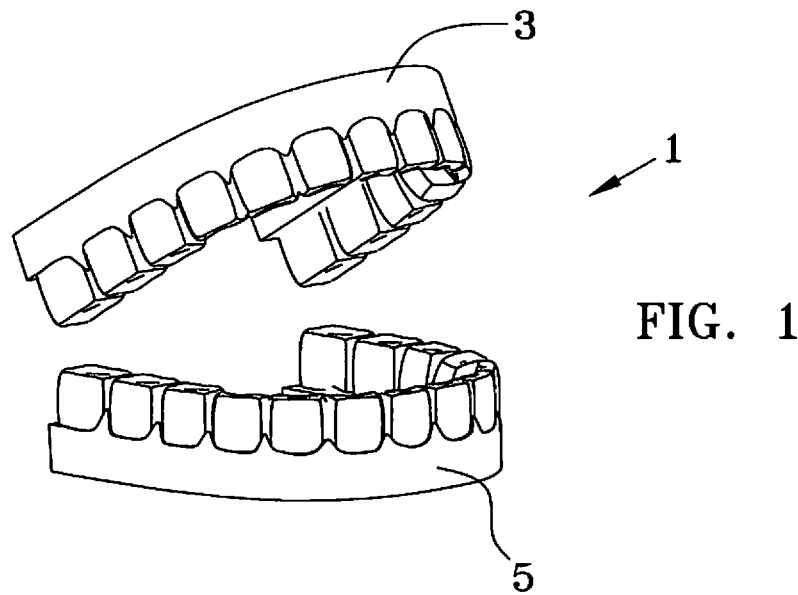
FIG. 1 is a left-side perspective view of an open dental model.

While various aspects and features of certain embodiments have been summarized above, the following detailed description illustrates at least on exemplary embodiment in further detail to enable one skilled in the art to practice such an embodiment. The described example is provided for illustrative purposes and is not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. While various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

In this description, the directional prepositions of up, upwardly, down, downwardly, front, back, top, upper, bottom, lower, left, right and other such terms refer to the device as it is oriented and appears in the drawings and are used for convenience only; they are not intended to be limiting or to imply that the device has to be used or positioned in any particular orientation. Distal in all instances shall refer to components or component parts located at the back of the mouth and proximal shall refer to components or component parts located at the front of the mouth.

Unless otherwise indicated, all numbers herein used to express quantities, dimensions, and so forth, should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

As used herein, the term "curved intrusive vector force application means" is to be interpreted according to 35 USC § 112 [para] 6. It refers to orthodontic devices that apply a curved or arced pushing force that can be transmitted to the upper and lower dental arches for the correction of Class II or Class III malocclusions.

As used herein the term "aligner" refers to a polymer sheath that is custom fit over all or part of the upper and lower teeth sets, and can be removed by the user. Its primary purpose is to retain some or all of the upper and lower teeth in a specific position in the mouth and relative to each other for the treatment of Class I malocclusions. It may be coupled to an orthodontic vector force application means for the combined treatment of Class II or Class III malocclusions simultaneously with Class I malocclusions.

As used herein the term "anchor sheath" refers to a polymer sheath that is custom fit for frictional engagement over all or some of the teeth in the upper ach and lower arch teeth sets, and can be removed by the user. Its purpose is to allow the teeth to serve as anchor points for the attachment of an orthodontic curved intrusive vector force application means used for the treatment of Class II or Class III malocclusions, thereby allowing the curved intrusive vector forces of the apparatus to be applied to the jaws. An aligner is one type of anchor sheaths that also serves to treat Class II or Class III malocclusions simultaneously with Class I malocclusions.

The term "curved intrusive vector force application apparatus" as used herein is a removable, adjustable force orthodontic device comprised of a curved intrusive vector force application means, operably attached to a pair of upper dental arch and lower dental arch anchor sheaths.

The present invention relates to a novel design for a removable, adjustable curved intrusive vector force application means mated to a removable custom fit sheath, anchored onto the outer faces of all or some of the teeth comprising the upper and lower dental arches.

Figure 14:
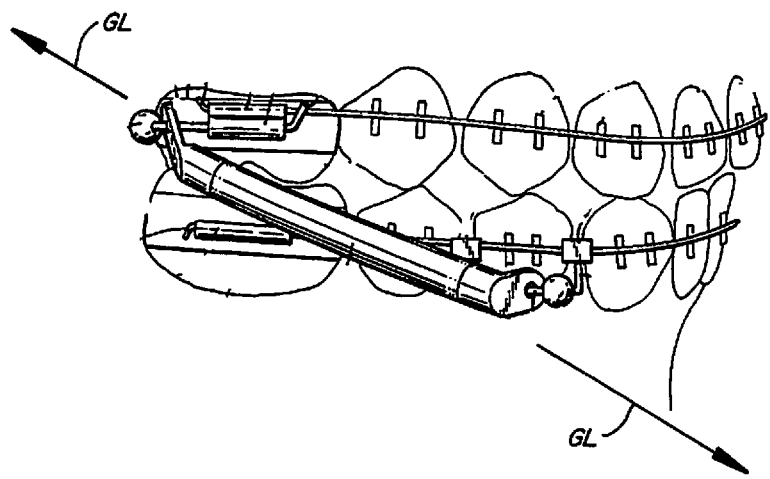
FIG. 14 is an example of a prior art orthodontic linear vector force application apparatus.

Mechanical devices to impart linear vector forces on both braces and also on anchor sheaths (also known as removeable retainers or aligners such as Invisalign®) are well documented in the 30 year old U.S. Pat. No. 4,708,646 by the present inventor. (Hereinafter the '646 patent.) This prior art utilized elongated linear members anchored onto both the patient's teeth or anchor sheaths to impart linear vectors of force onto the jaws of the patient to correct overbite situations. These vector forces can best be seen looking at the force lines designated GL on FIG. 14 from the prior art '646 patent of Dr. Jasper.

Figure 15:
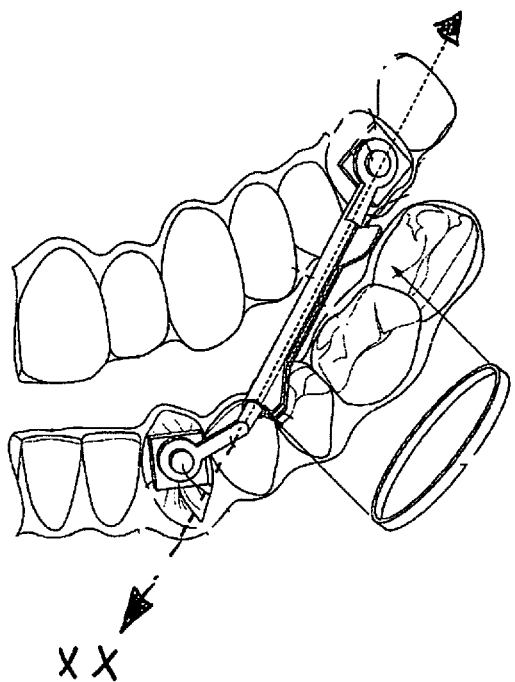
FIG. 15 is another example of a prior art orthodontic linear vector force application apparatus.

The device worked well when coupled to the teeth directly (braces) and became known industry wide as the "Jasper Jumper". However, it did not work on anchor sheaths (plastic aligners) because the line of the vector force applied was linear and caused the upper jaw to tip and the front of the anchor sheath to dislodge. Simply stated, there was not enough gripping force in the anchor sheath to overcome the vector forces for overbite correction and as a result the plastic aligners would dislodge from the anterior teeth. An example of such linear vector forces XX applied to anchor sheaths through linear members, for orthodontic correction of overbite, can be seen in FIG. 15, US Patent Application 2016/0067014, to Kottemann.

Figure 16:
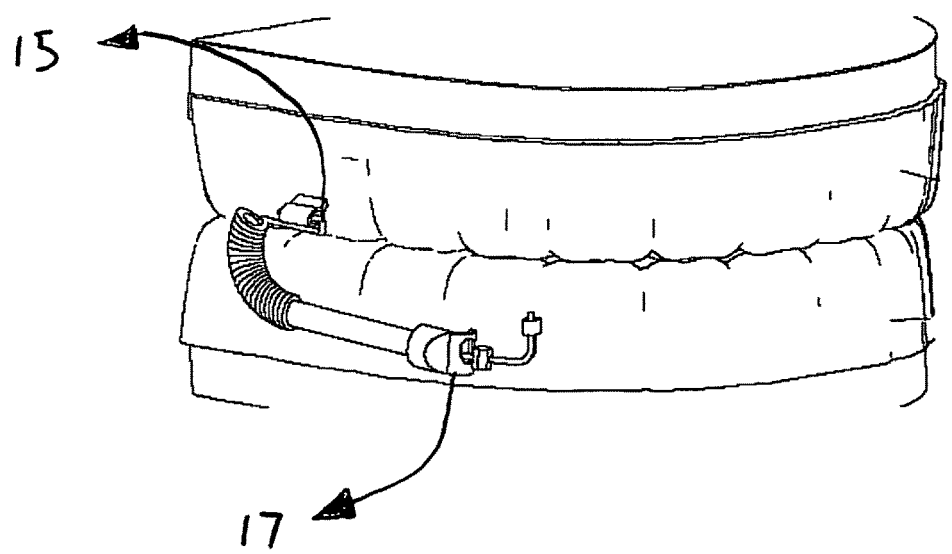
FIG. 16 is a perspective view of the curved intrusive vector forces applied through anchor sheaths.

The present curved intrusive vector force device applies curved intrusive vectors into use with aligners (anchor sheaths) so as not to not tip the upper jaw and keep the aligner on the teeth so that the device can do its job. This novel difference can be seen in the sweeping arcs of the applied vector forces as rays 15 and 17 of FIGS. 5 and 16. Thus, the introduction and mating of curved intrusive force vectors onto anchor sheaths while implementing the proper corrective pressures also has the unexpected result of helping the anchor sheaths stay on the patient's teeth so they can do their intended job of correcting the dental malocclusions.

Although the mating of corrective dental appliances with straight line vector forces onto aligners has been taught in the referenced prior art of Kottemann (US 2016/0067014) and decades ago by the present inventor himself, the use of such appliances that impart curved intrusive vectors has not. It is a novel concept that allows the aligners to stay in place while the arced, sweeping direction of the device's applied forces gently urge the jaws into the correct alignment.

FIG. 1 shows a perspective view of the upper dental arch 3 and the lower dental arch 5 of the dental model 1. The upper anchor sheath 40 and lower anchor sheath 42 (FIG. 2) are tightly form fitted sheaths that encapsulate the other surfaces of some or all of the teeth in the dental arches with a thin layer of medical grade polymer (preferably clear). The anchor sheaths are slightly flexible to accommodate their installation and removal, and are generally made from a set of castings taken of the user's teeth. The thickness of the anchor sheaths varies at different points and may be thickened in the areas to receive imbeds as necessary to ensure a secure affixation.

Referring generally to FIGS. 2-9 two embodiments of an orthodontic curved intrusive vector force application apparatus 10 (FIG. 3) (hereinafter "apparatus") according to the present invention, is connected to both the upper dental arch 3 (maxillary jaw) and the lower dental arch 5 (mandibular jaw) by placement of their anchor sheaths 40 and 42 over the teeth of the upper and lower dental arches 3 and 5. Each anchor sheath 40 or 42 may be formed to fit the patient's mouth and extend over whatever number of teeth are required to provide a firm anchor for the sweeping, arced pushing forces used to facilitate the correction desired.

Figure 2:
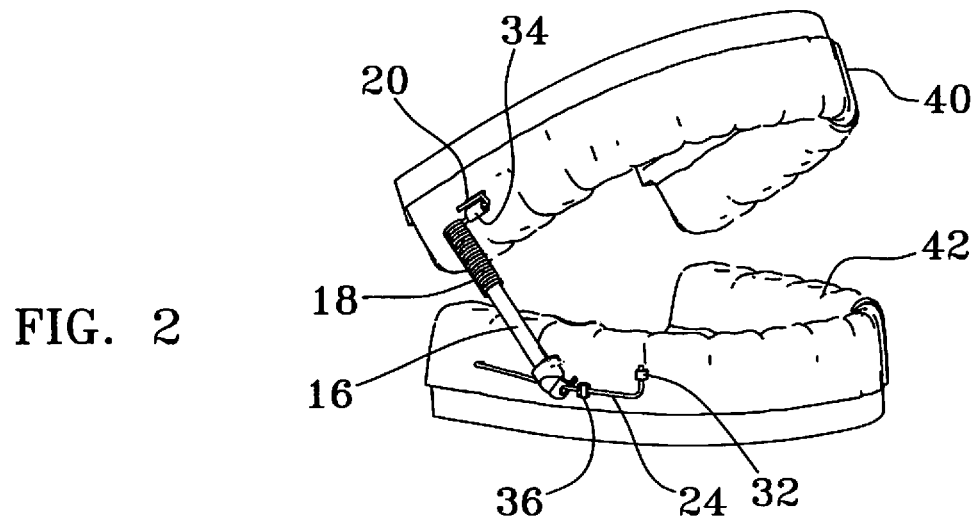
FIG. 2 is a left-side perspective view of the orthodontic vector force application apparatus installed on an open dental model for overbite correction.
Figure 3:
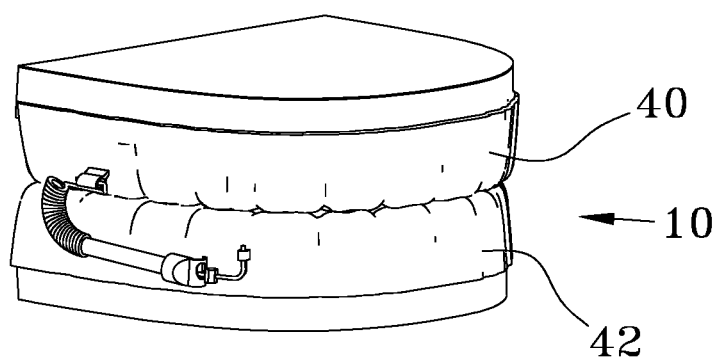
FIG. 3 is a left-side perspective view of the orthodontic vector force application apparatus installed on a closed dental model for overbite correction.
Figure 4:
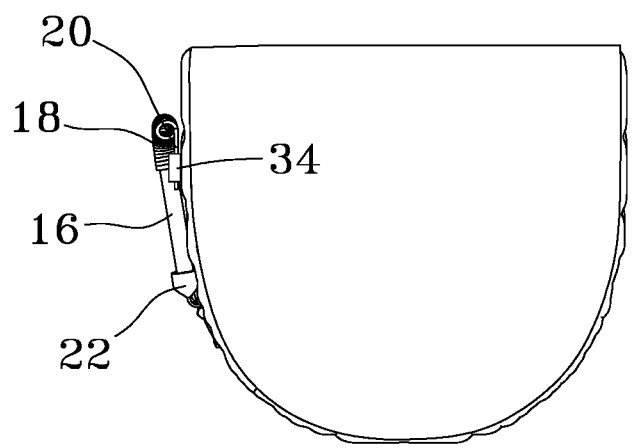
FIG. 4 is a top view of the orthodontic vector force application apparatus installed on a closed dental model for overbite correction.
Figure 6:
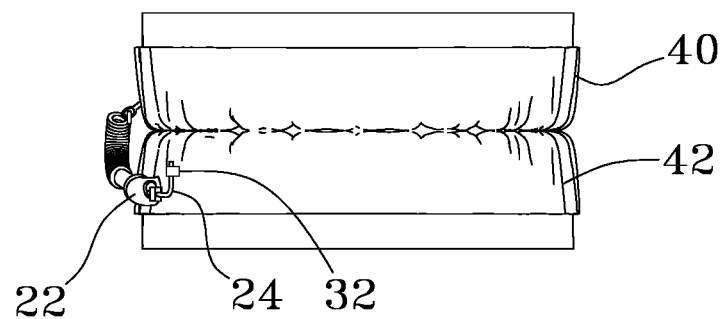
FIG. 6 is a front view of the orthodontic vector force application apparatus installed on a closed dental model for overbite correction.
Figure 7:
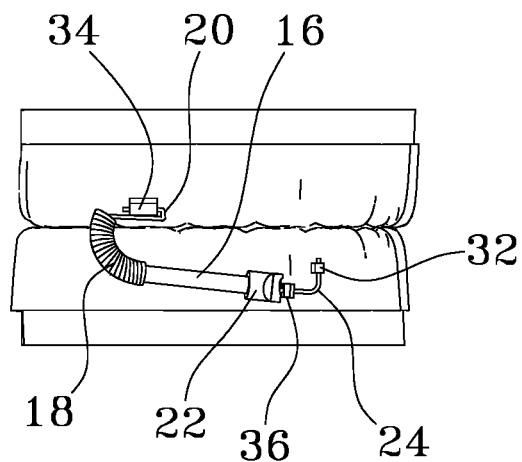
FIG. 7 is a right-side view of the orthodontic vector force application apparatus installed on a closed dental model for overbite correction.
Figure 8:
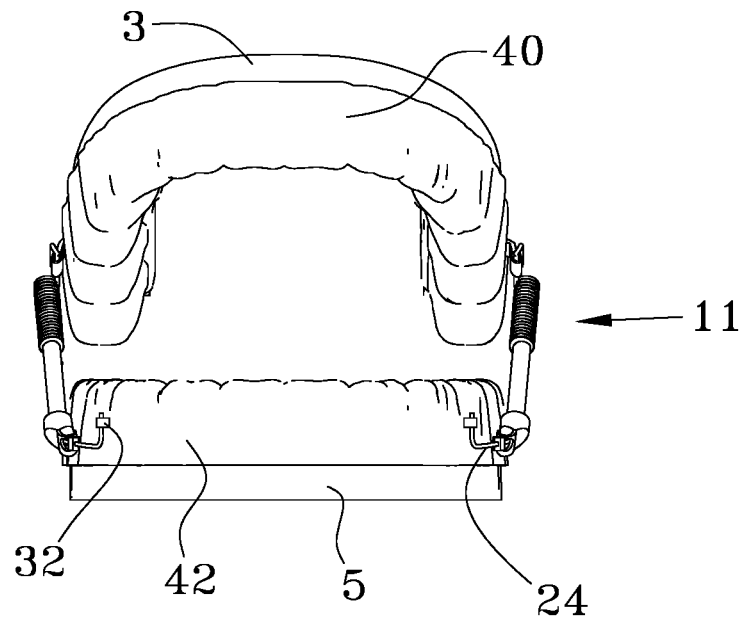
FIG. 8 is a front view of the orthodontic vector force application apparatus installed on an open dental model for overbite correction.
Figure 9:
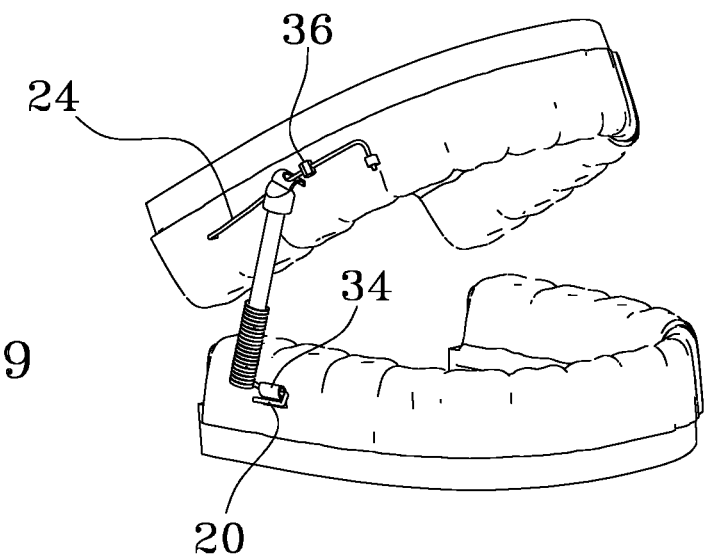
FIG. 9 is a side perspective view of the orthodontic vector force application apparatus installed on an open dental model for underbite correction.

Turning to FIGS. 2 and 8, apparatus 10 is shown in its passive state and can be seen comprised of an upper anchor sheath 40 a lower anchor sheath 42, a pair of curved vector vector force application means 11 (FIGS. 10-12), a pair of guide wires 24, at least one pair of guide wire imbed anchors 32, a pair of attachment wire imbed anchors 34, and a locking stop 36. FIGS. 3, 6 and 7 illustrate the apparatus 10 in its active state.

As can be seen in FIGS. 10-13 the curved intrusive vector force application means 11 of the preferred embodiment is made of rigid linear member 16, a force generating curved vector control module 18, a rear attachment wire 20, and attachment member 22. Preferably, rigid linear member 16 is made of 3/32 (0.093 inch) stainless steel and is elliptical in shape, although in alternate embodiments it my round as well. It has a distal end and a proximal end. Shown in enlarged cross-section, (FIG. 13) the elliptical shape is clearly visible. It should be noted that rigid member 16 can be made of different rigid materials including steel or plastic, and can have other cross sections including circular, square, rectangular, and flat. While illustrated as a tube (hollow), rigid member 16 could also be solid in construction.

Curved intrusive vector control module 18, is an elliptical or circular shaped torsion spring, preferably coiled from a rectangular, or round wire, which is an alloy of stainless steel containing Cobalt, Chromium, and Nickel, that is able to be formed in its soft state and then heat treated to create spring steel. However, any variety of metals can be used to fabricate the coil, including Nickel Titanium. Durability and the ability to deliver the forces in the range of 3 to 8 ounces are the main factors for choosing the appropriate material from which to form the vector control module 18. Specifically, and preferably, 0.025 inch stainless steel, round wire has produced the desired forces of 4 to 8 ounces pressure. Practical experience has shown that approximately 3.5 ounces of pressure corrects Class II and III malocclusions with the proper balance between comfort and corrected wearing time.

The elliptical shape of both the rigid member 16 and curved intrusive vector control module 18 increases patient comfort, since the elliptical shape allows the minor axis of rigid member 16/curved intrusive vector control module 18 to reside in the horizontal plane between the patient's gum line and cheek, while providing increased strength, since the major axis resides generally perpendicular to the gum line. The elliptical shape provides the perfect combination of comfort, food flow, and strength. It is to be noted that circular shaped rigid members are used in alternate embodiments. Variations of the structure of the rigid member 16 and curved intrusive vector control module 18 can accomplish the desired results provided that the end of rigid member 16 that is affixed to curved intrusive vector control module 18 is matingly configured to accept the end of the curved intrusive vector control module 18. For example, a rectangular solid linear member with an elliptical mounting-end (or circular mounting-end for a cylindrical coil) would meet the necessary structural requirements.

Curved intrusive vector control module 18 is soldered, welded, or glued to the distal end of rigid linear member 16, such that curved intrusive vector control module 18 comprises approximately 50-70% of the length of apparatus 10. To give an idea of size, rigid member 16 is approximately 12 mm long, while the curved intrusive vector control module is approximately 24 mm long. These lengths are simply an approximation as apparatus 10 will be made in different lengths (small, medium, and large) to accommodate different sized mouths. However, the curved intrusive vector control module will still comprise approximately 50-70% of the length of apparatus 10, keeping the flex point (located at the approximate midpoint of the torsion spring) of the vector control module 18 to the distal 45-60% of apparatus 10. It is to be noted that the curved intrusive vector forces swing an arc with the inner end of its radius at the flexpoint of the torsion spring. This flexpoint of the torsion spring would generally occur at the approximate midpoint along its length except where the rigid linear member extends a length into the interior of the front end of the torsion spring thereby stiffening the vector control module such that its flex point is shifted away from the midpoint and towards the distal end of the torsion spring.

In an alternate embodiment, with a circular cross sectional (cylindrical) curved intrusive vector control module, a circular mounting end would be formed on the elliptical rigid member to serve as a connection point to the cylindrical curved intrusive vector control module.

Continuing with FIGS. 10-12, rear attachment wire 20 is an unwound extension of the wire comprising the curved intrusive vector control module 18. It extends normally from the linear axis of the vector control module 18. Attachment member 22 is for adjustable connection with guide wire 24 which is imbededly connected (in either of two ways as disclosed herein) at its proximal (front) and distal (rear) end to one of the anchor sheaths 40 or 42. For quick yet secure attachment with guide wire 24, attachment member 22 has a flat portion 26, which resides at an orientation of approximately 90° from the longitudinal axis of apparatus 10. Attachment member 22 is soldered, welded, or glued to rigid member 16, and can be made of stainless steel, or any rigid, durable material including steel or plastic.

It is to be noted that in alternate embodiments, portion 26 may contain an optional receiving slot 30 that runs from the central orifice 28 to the peripheral edge of the portion 26. This slot 30 allows the apparatus 10 to be removed or installed without removing the guide wire 24 as was previously required with prior art appliances. The slot can be squeezed to close around the guide wire 24 in the installation process.

Moving the flex point of apparatus 10—that is the approximate midpoint of the curved intrusive vector control module 18, to the distal 50-70% of the apparatus's 10 length accomplishes three things: 1) it cannot bend between the teeth to be chewed on and broken, 2) it causes rigid member 16 to reside below the food bolus area 13 (See FIG. 3) to make eating more comfortable, and 3) the curved intrusive force vectors generated by the installed orthodontic apparatus 10 result in correction of the most severe overbites/underbites. Prior art appliances flexing at the midpoint of the appliance and having a hinge at the upper distal end, place linear vectors on the upper and lower jaws, rather than the sweeping arced vectors of the apparatus 10.

In the case of the apparatus 10 used for overbite correction, (FIGS. 2, 3, 4, 6, 7 and 9) the curved intrusive vector force application means 11 is operatively connected to the upper anchor sheath 40 by an attached wire imbed anchor 34. This is a hollow tubular section of metal affixed along its side to a small backing member (preferably a planar member) that is cast into the distal region of the upper anchor sheath with the linear axis residing approximately parallel to the linear axis of the upper anchor sheath 40. (In the preferred embodiment, anchoring teeth clasps that are commonly used to hold retainers in place and are well known and embody this structure.) Its backing member is fully imbedded in the polymer of the anchor sheath such that there are no abrasive sections of the backing member extending from the inner surface of the upper anchor sheath 40. The attached wire imbed anchor 34 is sized for the internal passage of attached wire 20 therethrough. In this way the attachment wire 20 may be passed through the inside of the imbed anchor 34 and bent back 180 degrees around the outside of the imbed anchor 34 to secure it to the upper anchor sheath 40.

The curved intrusive vector force application means 11 is operatively connected to the lower anchor sheath 42 by attachment to guide wire 24 as discussed further herein. The guide wire 24 is rigid wire that connects in a spaced configuration along the outside of the lower anchor sheath 42 at proximal and distal sections of the lower anchor sheath 42. This spaced configuration off of the side of the lower anchor sheath 42, allows for the adjustment and the sliding movement of the attachment member 22 along the guide wire 2. In its preferred embodiment this guide wire 24 has an approximately right angle bend at its proximal end where it is secured to the guide wire imbed anchor 32. This minimizes interference between the operative parts such as the guide wire imbed anchor 32.

The guide wire imbed anchor 32 utilized at the proximal end of the guide wire 24 and the bottom anchor sheath 42, is essentially another variation of the attached wire imbed anchor 34, but sized accordingly. Its method of attachment to the proximal end of the guide wire 24, however, differs. The proximal end of the guide wire 24 is placed through a bore in the guide wire imbed anchor 32 and mechanically crimped, soldered, glued or permanently affixed by any equivalent means to the guide wire imbed anchor 32. With the bend in the guide wire 24 on one side of the guide wire imbed anchor 32 on the other, the guide wire 24 is securely anchored. The guide wire imbed anchor 32 has a hollow tubular construction, and similar to the attached wire imbed anchor 34 may have a backing member cast into the polymer thickness of the lower anchor sheath 42. In other embodiments a direct implant of the guide wire into the polymer of the anchor sheath (upper or lower) will also work.

The distal end of the guide wire 24 is illustrated attached to the lower anchor sheath 42 by a direct imbed of its plain end (after an approximate 90 degree bend) into the polymer material the anchor sheaths are formed from. At the distal ends of the anchor sheaths the wall thickness is greater than at the proximal end and such a direct imbed is sufficient to retain the distal end of the guide wire 24.

It is to be noted that the guide wire 24 may be affixed to the lower anchor sheath 42 at both its proximal and distal ends by guide wire imbed anchors 32 or it may be affixed to the lower anchor sheath 42 by a direct imbed of the end of the guide wire into a thickened section of the lower anchor sheath 42. Either of the different style of imbeds discussed herein may be utilized in any imbed location of the anchor sheaths and will vary with different manufacturers. The embodiments herein utilize guide wire imbed anchors 32 on the front anchor points of the guide wires 24 and a direct guide wire imbeds on the rear anchor points of the guide wires 24, for illustrative purposes only.

The locking stop 36 of the preferred embodiment is an adjustable locknut with an orifice extending axially through its body perpendicular to the travel of its threaded nut. It's orifice is dimensionally sized for slide positioning along the length of the guide wire 24 so as to constrain the forward movement of the curved intrusive vector force application means 11 along the side of the lower anchor sheath 42 when its nut is tightened against the guide wire 24. The locknut 36 is positioned towards the distal end of the guide wire 24 to increase the pushing pressure of the apparatus 10 when it is in its active state and the proximal end of the vector force application means 11 abuts the locknut 36. As the patient's malocclusion is slowly corrected and the jaws align better, the curved intrusive vector force application means 11 flexes less and the amount of corrective pressure is reduced. At this time the locknut 36 is loosened, drawn backwards away from the front of the mouth along the guide wire 24 and tightened in a position that will have the vector force application means 11 exert approximately 3.5 oz of pushing pressure when in the active position. It is to be noted that although the pushing pressure of the curved intrusive vector force application means serves to provide the corrective forces to correct the Class II or III malocclusions, an unexpected result of the design of the apparatus is that the pushing intrusive forces also help maintain the upper and lower anchor sheaths 40 and 42 onto the patient's teeth.

Figure 5:
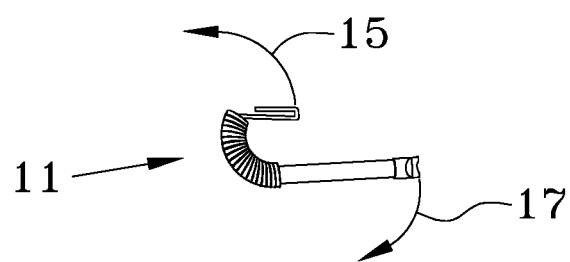
FIG. 5 is a left-side view of the orthodontic vector force application apparatus in its flexed state; the curved rays illustrating the path required for the appliance to return to its passive (unflexed) state.

This apparatus 10 provides an enormous improvement over the prior art for several reasons. First, it does not require the direct attachment to a set of braces affixed onto the patient's teeth, allowing those without braces for Class I malocclusions to wear them. Second, it is removable for temporary periods by the patient themselves. Third, it does not deliver its force straight along its axis to the distal side of the molars. Fourth the device imparts the curved vector forces so as to retain the anchor sheaths on the patient's teeth. Attachment wire 20 is connected directly to the vector control module 18 without a hinge, allowing apparatus 10, as shown in FIG. 3, to return to its passive, pre-installed state (FIG. 2) in a sweeping motion 15, (FIG. 5) lifting up on the front (closest to the mouth opening) of the molar tube, while ray 17 illustrates the sweeping force placed on the mandible. This curved intrusive vector force thus prevents the upper jaw from tipping therein preventing dislodging of the front of the anchor sheath. This was a problem with the linear vector forces applied through the prior art orthodontic apparatuses. This is best illustrated in FIG. 5 which shows apparatus 10 in its installed shape—that is, the same shape that can be seen in FIG. 3. The non-linear rays, 15 and 17, indicate the direction apparatus 10 moves in order to return to its pre-installed/passive state. As can be seen, the distal and proximal ends of the curved intrusive vector force application apparatus 10 apply their sweeping corrective forces in arcs having a radius originating at the midpoint of the flexed (bent) curved vector control module 18. These rays 15 and 17, indicate the curved intrusive vector forces that the apparatus imparts to the teeth and jaws. While FIG. 5 is not a free body diagram, it is not hard to imagine while looking at FIG. 5 in conjunction with FIG. 3, how apparatus 10 lifts up on the front of the molar tube causing the roots (not illustrated) of the upper molars to tip toward the back of the mouth prior to the whole tooth moving distal. Since the molars are connected to the front teeth via the guide wire 24 anchored into the lower anchor sheath 42, intrusive and backward curved vectors are placed on the upper incisors. The mandubular front teeth receive an equal and opposite force, shown in FIG. 5 as ray 17 illustrated pushing downwards and forward on these teeth, intruding them to compensate for their overbite condition.

Functionally, as installed in FIGS. 2-8, apparatus 10 will reposition the upper dental arch 12 by placing forces on the upper molars (maxillary), causing their root tips (not illustrated) to move backwards (that is towards the back of the throat) first, putting curved intrusive vector forces on the front upper and lower incisors, keeping the apparatus 10 on the patient's teeth and over a period of months correcting even the most severe overbites (Class II malocclusions).

The majority of this disclosure discusses and illustrates use of the apparatus 10 for treatment of a Class II malocclusion or overbite condition. For use in a Class III malocclusion or underbite condition, (FIG. 9) the above apparatus 10 is simply inverted (or worn upside down) with respect to the connection of the guide wire 24 and the vector force application means 11 to the anchor sheaths. Here the guide wire 24 is affixed to the upper anchor sheath 40 and the distal end of the curved intrusive vector force application means 11 is affixed to the rear of the lower anchor sheath 42. Connection of the curved intrusive vector force application means 11 to the guide wire 24 is identical where attachment member 22 at the proximal end of the curved intrusive vector force application means 11 slides onto the guide wire 24 via its receiving slot 29 (which is squeezed to close) and the pressure adjusted via locknut 36. However, the rear attachment wire 20 of the curved intrusive vector force application means 11 is connected to the lower anchor support 42 by an imbed anchor around which the rear attachment wire 20 is bent around.

Once installed, appliance 10 will push the lower dental arch 14 backwards, and provide pushing vectors on the upper front teeth, resulting in the repositioning of the maxilla to the desired position. Functionally, in this configuration apparatus 10 will reposition the lower dental arch 5 by placing forces on the lower molars, causing their root tips (not illustrated) to move distally (that is towards the front of the throat) first, putting intrusive forces on the front upper and lower incisors, and over a period of months correcting even the most severe Class III malocclusions.

Although not illustrated herein, the anchor sheaths 40 or 42 need not extend over all of the teeth in either of the dental arches, rather it can resemble a partial aligner or partial plate. The anchor sheaths need only encapsulate enough teeth to gently urge the jaws into their corrective position without affecting the spacing or slat of the encapsulated teeth.

The method of applying curved vector forces for the correction of Class II or Class III malocclusions is best detailed in the following steps:

Assemble two curved intrusive vector force application means by connecting a rigid linear member coupled to a front attachment member, to a curved intrusive vector force control module (torsion spring) with a rear attachment wire, wherein the midpoint (flexpoint) of the curved intrusive vector force control module lies in a distal region that is 50-70% of the distance between the proximal and distal ends of the overall length of the curved intrusive vector force application means;

Assemble a removable first anchor sheath having a pair of linear guide wires embedded at their distal and proximal ends in the first anchor sheath and extending from the anchor sheath's sides;

Assemble a removable second anchor sheath having a pair of guide wire imbed anchors extending therefrom;

Install a locking stop onto each of the linear guide wires;

Install the distal end of each curved intrusive vector force application means to the guide wire imbed anchors on the second anchor sheath by bending their rear attachment wires about the wire imbed anchors;

Install the proximal end of each curved intrusive vector force application means to the guide wires on the first anchor sheath by putting the attachment member of the linear member around the guide wire between the locking stop and the distal ends of the guide wires;

Adjust and lock the position of the locking stop along the guide wires so as to abut the attachment member and force the proximal end of the curved intrusive vector force application means down the guide wires toward the rear of the mouth such that there is between 3 and 8 ounces of force required to flex the curved intrusive vector force control module at an approximate right angle;

Install over a portion of the teeth in a first dental arch, the removable first anchor sheath while installing over a portion of the teeth in a second dental arch, the removable second anchor sheath; and As the patient's jaws are brought into alignment, continually adjust and lock the position of the locking stop as above to maintain the 3 to 8 ounces of force required to flex the curved intrusive vector force control module at an approximate right angle.

While certain features and aspects have been described with respect to exemplary embodiments, one skilled in the art will recognize that numerous modifications are possible. For example, while various methods and processes described herein may be described with respect to particular structural and/or functional components for ease of description, methods provided by various embodiments are not limited to any particular structural and/or functional architecture, but instead can be implemented on any suitable dental appliance configuration. Similarly, while certain functionality is ascribed to certain system components, unless the context dictates otherwise, this functionality can be distributed among various other system components in accordance with the several embodiments.

Consequently, although several exemplary embodiments are described above, it will be appreciated that the invention is intended to cover all modifications and equivalents within the scope of the following claims.

I claim:

1. A method for applying curved vector forces to the upper dental arch and lower dental arch for the correction of class II and class III malocclusions, comprising the steps of:
   assembling two curved intrusive vector force application means by connecting a rigid linear member coupled to a front attachment member, to a torsion spring with a rear attachment wire, wherein a flexpoint of the torsion spring lies in a distal region that is 50-70% of a distance between a proximal end and a distal end of said curved intrusive vector force application means;
   assembling a removable first anchor sheath having a pair of linear guide wires extending from a right side and a left side of said first anchor sheath;
   assembling a removable second anchor sheath having a pair of guide wire imbed anchors extending therefrom;
   installing said distal end of each curved intrusive vector force application means to said guide wire imbed anchors on said second anchor sheath;
   installing said proximal end of each curved intrusive vector force application means to said guide wires on said first anchor sheath;
   affixing said front attachment member at a position along said guide wires such that there is between 3 and 8 ounces of force flexing said torsion spring and pivoting said first anchor sheath away from said second anchor sheath about a radius centered at a flexpoint along said torsion spring prior to the installation of said first anchor sheath and said second anchor sheath over a portion of teeth in said first dental arch and said second dental arch; and
   treating class II malocclusions by installing said removable first anchor sheath over a portion of teeth in said first dental arch while installing said removable second anchor sheath over a portion of teeth in said second dental arch or treating class III malocclusions by installing said removable first anchor sheath over a portion of teeth in said second dental arch while installing said removable second anchor sheath over a portion of teeth in said first dental arch.

2. The method for applying curved vector forces to the upper dental arch and lower dental arch for the correction of class II and class III malocclusions of claim 1, comprising the additional steps of:
   installing a locking stop onto each of said linear guide wires;
   affixing said locking stop at a position along said guide wires so as to continually abut said attachment member and sliding said curved intrusive vector force application means along said guide wires toward said distal end of said guide wires such that there is between 3 and 8 ounces of force required to flex said curved intrusive vector force application means, pivoting said first anchor sheath and said second anchor sheath about said midpoint of said torsion spring.

3. The method for applying curved vector forces to the upper dental arch and lower dental arch for the correction of class II and class III malocclusions of claim 2, comprising the final steps of:
   periodically self-adjusting and locking said position of said locking stop to maintain said 3 to 8 ounces of force required to flex said curved intrusive vector force control module at a right angle as the patient's jaws are brought into alignment.

4. A method for applying curved vector forces to the upper dental arch and lower dental arch for the correction of class II and class III malocclusions, comprising the steps of:
   assembling two curved intrusive vector force application means by connecting a rigid linear member coupled to a front attachment member, to a torsion spring with a rear attachment wire, wherein a midpoint of the torsion spring lies in a distal region that is 50-70% of a distance between a proximal end and a distal end of said curved intrusive vector force application means;
   assembling a removable first anchor sheath having a pair of linear guide wires extending from a right side and a left side of said first anchor sheath;
   assembling a removable second anchor sheath having a pair of guide wire imbed anchors extending therefrom;
   installing a locking stop onto each of said linear guide wires;
   installing said distal end of each curved intrusive vector force application means to said guide wire imbed anchors on said second anchor sheath by affixing said rear attachment wires about said wire imbed anchors;
   installing said proximal end of each curved intrusive vector force application means to said guide wires on said first anchor sheath by connecting said attachment member of said linear member onto said guide wire between said locking stop and a distal end of said guide wires;
   affixing said locking stop at a position along said guide wires so as to abut said attachment member and force said proximal end of said curved intrusive vector force application means along said guide wires toward said distal end of said guide wires a such that there is between 3 and 8 ounces of force required to flex said curved intrusive vector force application means at a right angle, pivoting said first anchor sheath and said second anchor sheath about said midpoint of said torsion spring; and
   treating class II malocclusions by installing said removable first anchor sheath over a portion of teeth in said first dental arch while installing said removable second anchor sheath over a portion of teeth in said second dental arch or treating class III malocclusions by installing said removable first anchor sheath over a portion of teeth in said second dental arch while installing said removable second anchor sheath over a portion of teeth in said first dental arch.

5. The method for applying curved vector forces to the upper dental arch and lower dental arch for the correction of class II and class III malocclusions of claim 4, comprising the additional last step of:
   periodically self adjusting and locking said position of said locking stop to maintain said 3 to 8 ounces of force required to flex said curved intrusive vector force control module at a right angle as the patient's jaws are brought into alignment.

* * * * *